US00PP23853P2

(12) United States Plant Patent
Hurd

(10) Patent No.: US PP23,853 P2
(45) Date of Patent: Aug. 27, 2013

(54) ***VERONICA* PLANT NAMED 'HOCUS POCUS'**

(50) Latin Name: *Veronica spicata*
Varietal Denomination: Hocus Pocus

(75) Inventor: Kevin A. Hurd, Chicago, IL (US)

(73) Assignee: Walters Gardens, Inc., Zeeland, MI (US)

( * ) Notice: Subject to any disclaimer, the term of this patent is extended or adjusted under 35 U.S.C. 154(b) by 141 days.

(21) Appl. No.: 13/135,550

(22) Filed: Jul. 8, 2011

(51) Int. Cl.
*A01H 5/00* (2006.01)

(52) U.S. Cl.
USPC ..... Plt./251

(58) Field of Classification Search
USPC ..... Plt./251
See application file for complete search history.

*Primary Examiner* — Susan McCormick Ewoldt

(57) ABSTRACT

The new and distinct cultivar of ornamental Spiked Speedwell *Veronica spicata* 'Hocus Pocus' with compact habit with stiff upright to slightly-curved branched spikes producing vivid violet-purple flowers over a long period and suitable as a potted plant, for the garden, and for cut flower arrangements.

1 Drawing Sheet

Botanical classification: *Veronica spicata.*
Variety denomination: 'Hocus Pocus'.

BACKGROUND OF THE INVENTION

The present invention relates to the new and distinct cultivar of Spiked Speedwell, botanically known as *Veronica spicata* 'Hocus Pocus', and hereinafter referred to as the cultivar 'Hocus Focus' or the "plant". The new plant originally referenced as breeder code "06-01" was hybridized in the summer of 2006 by Kevin A. Hurd in the hybridizing greenhouses of a nursery in Zeeland, Mich., USA, as an open pollination of *Veronica spicata* 'Foxy Lady' U.S. Plant Pat. No. 20,679. The plant has been asexually propagated by shoot tip cuttings at the same nursery in the greenhouses in Zeeland, Mich., with subsequent asexually propagated plants found to be identical to the original selection with all the same traits as the original seedling.

BRIEF SUMMARY OF THE PLANT

*Veronica spicata* 'Hocus Pocus' is unique from all other Spiked Speedwell known to the inventor. Several other cultivars have blue to purple flowers, but this is the only variety known by the applicant to have the following trait combinations.

The closest comparison varieties are *Veronica* 'Glory' U.S. Plant Pat. No. 18,932, *Veronica* 'Sunny Border Blue' (not patented), *Veronica* 'Goodness Grows' (not patented), *Veronica* 'Atomic Violet' U.S. Plant Pat. No. 21,780 and *Veronica* 'Red Fox' (not patented). The new plant has more purple flowers than 'Goodness Grows', and is shorter than 'Sunny Border Blue' 'Atomic Violet' and 'Glory'. 'Giles Van Hees' (not patented) and the female parent 'Foxy Lady' are both more pink in flower.

VERONICA COMPARISON

| Cultivar | Petal Color | Scape Height |
|---|---|---|
| 'Atomic Violet' | dark purple-violet | 48 to 50 cm |
| 'Goodness Grows' | blue | 30 to 35 cm |
| 'Foxy Lady' | fuchsia pink and white | 30 to 35 cm |
| 'Giles Van Hees' | bright pink | 15 to 20 cm |
| 'Hocus Pocus' | vivid violet-purple | 35 to 40 cm |
| 'Royal Candles' | violet-blue | 38 to 46 cm |
| 'Sunny Border Blue' | violet-blue | 45 to 60 cm |

The following are traits of *Veronica spicata* 'Hocus Pocus' that in combination distinguish it from all other Spiked Speedwell know to the inventor:

1. Compact habit with stiff upright to slightly-curved spikes above dense mats of foliage.
2. Scapes with numerous flowers of distinctly vivid violet-purple petals.
3. Branched peduncles with long blooming season.

BRIEF DESCRIPTION OF THE DRAWINGS

The photograph of the new plant demonstrates the overall appearance and unique traits of 'Hocus Pocus' as a one-year old plant grown in greenhouse. The colors are as accurate as reasonably possible with color reproductions. Variation in ambient light spectrum, source and direction may cause the appearance of minor variation in color.

FIG. 1 shows the plant in full flower.

DETAILED BOTANICAL DESCRIPTION

The following descriptions and color references of a greenhouse-grown one-year old plant of 'Hocus Pocus' are based on the 2001 edition of The Royal Horticultural Society Colour Chart except where common dictionary terms are used. *Veronica spicata* 'Hocus Pocus' has not been observed under all possible environments. The phenotype may vary slightly with different growing environments such as temperature, light, fertility, soil pH, moisture and maturity levels, but without any change in the genotype. The following observations and size descriptions are based on two-year old plants in the full sun trial garden of a nursery in Zeeland, Mich. with supplemental fertilizer and water as needed.

Botanical classification: *Veronica spicata.*

Parentage: Female (seed parent) *Veronica spicata* 'Foxy Lady' U.S. Plant Pat. No. 20,679, male (pollen parent) unknown.

Plant habit: Hardy herbaceous perennial, compact, with several stems, 15 to 18 cm tall without scapes and 35 to 40 cm wide; flowering beginning late June in Michigan and continuing for about 6 weeks with occasional repeat if deadheaded.

Leaves: Simple, flat, elliptic to lanceolate, opposite, serrated, minutely pubescent below and above, acute apex, acute to attenuate base; about 7.5 cm long by 2.5 cm wide decreasing in both length and width distally.

Leaf color: Nearest RHS 137A on top, nearest RHS 138C below.

Veins: Reticulate, minutely pubescent below and above; main vein about 1.0 mm diameter at abaxial base and 0.5 mm at adaxial base.

Vein color: Adaxial surface base of center vein between RHS 144C and RNS 144B, gradually darkening within proximal one third to same color (RHS 137A) as leaf; on adaxial surface proximal one half of center vein and secondary veins closest to center vein on abaxial surface more yellow than RHS 144C and more green than RHS 151A.

Petiole: Simple, concaved upward on edges, minutely pubescent above and below; about 1.0 to 2.0 cm long (distally shorter) and 2.0 mm wide.

Petiole color: Adaxial side nearest RHS 138C in center and RHS 138A on margins; abaxial side between RHS 144C and RNS 144B in center and nearest RHS 138C on margins.

Buds two days prior to opening: Convolute, narrowly oblong, obtuse apex; about 5.0 mm long and 2.0 mm diameter.

Bud color: Nearest RHS 83B on distal one half lightening to lighter than RHS 91D in the second one quarter from base with the basal one quarter nearest RHS 145C.

Flowers: On heavily branched upright to slightly-curved spikes; numerous, approximately 200 per main spike; about 4.0 mm in across and about 6.0 mm deep; no detectible fragrance; flowers persist individually for 4 to 6 days whether on the plant or cut, self-cleaning.

Petals: Four, one larger petal above and three slightly small below, simple, entire, with rounded apex and fused in basal one half; larger petal about 5.0 mm long by 2.5 mm wide, smaller petals about 5.0 mm long and 2.0 mm wide; glabrous outer and inner sides except with 1.0 mm long hairs at inside base.

Petal color: Inside surface apex nearest RHS 83B and lightening to RHS 86C; outer surface nearest RHS86A on perimeter and RHS 86B in center; hair at base of throat lighter than RHS 85D.

Androecium:

*Filaments*.—Two, fused to lower portion of petal; about 4.0 mm by 0.2 mm; white, lighter than RHS 155D.

*Anther*.—Dorsifixed with anther ends bent back around filament in about a 270 degree angle; each half elliptic with acute apex, about 1.5 mm by 1.0 mm.

*Anther color*.—Variable, some between RHS 176B and more purple than RHS 182C at apex and lightening to more purple than RHS 174C at middle and base, others more yellow nearest RHS 162C in center with RHS 83B around perimeter.

*Pollen*.—Limited, globose, less than 0.1 mm; RHS 10D.

Gynoecium:

*Style*.—6.0 mm by 0.25 mm, RHS 83A at apex lightening to RHS 83C at base.

*Stigma*.—Cylindrical, 0.25 mm in diameter; persists after petals drop; RHS 83A.

*Ovary*.—Spherical, about 1.0 mm in diameter; nearest RHS 144A.

Sepals: Four, surface dull, ovate to narrowly ovate, acute apex, base fused forming corolla, sparsely pubescent with minute glandular hairs; upper pair about 2 mm long and 0.5 mm wide, lower pair about 3 mm long by about 0.5 mm wide, nearest RHS 137A both surfaces.

Peduncle: About 24 per plant; raceme, strong, erect to slightly curved, round, minutely pubescent to canescent; about 37 cm long and 3.0 mm in diameter at the base, flowering section of the main stem 18 to 22 cm long, averaging 20 cm long; diameter of flowering portion of raceme about 2 cm; freely branching at nearly every node; about 7 to 8 nodes; internode length about 2.5 cm.

Peduncle color: Nearest RHS 138B.

Pedicel: Upright, rigid, about 1.0 mm long and 0.5 mm wide, sparsely pubescent with minute hairs; nearest RHS 137A.

Bract: One, subtending each flower, linear, acute apex, mostly entire, sessile, based fused to peduncle, proximal bracts about 2.0 cm long and 2.0 mm wide and decreasing distally to about 3.0 mm long and less than 0.5 mm wide.

Bract color: RHS 137A above and RHS 137C below.

Fruit: Elliptic, about 1.0 mm long; between RHS 166A and RHS 166B.

Propagation: The plant roots from cuttings in about 2 weeks and finishes to flowering in a 3.8 liter container in 8 to 10 weeks following a vernalization period of about 8 weeks.

Hardiness, pest and disease resistance: The plant grows best with plenty of moisture and adequate drainage, but is able to tolerate some drought when mature. Hardiness at least from USDA zone 4 through 8. Disease and pest resistance beyond what is typical of that of other Spiked Speedwell has not been observed.

I claim:

1. A new and distinct cultivar of ornamental Spiked Speedwell plant, *Veronica spicata* 'Hocus Pocus', as herein described and illustrated, with compact habit with stiff upright to slightly-curved branched spikes producing vivid violet-purple flowers over a long period and suitable as a potted plant, for the garden, and for cut flower arrangements.

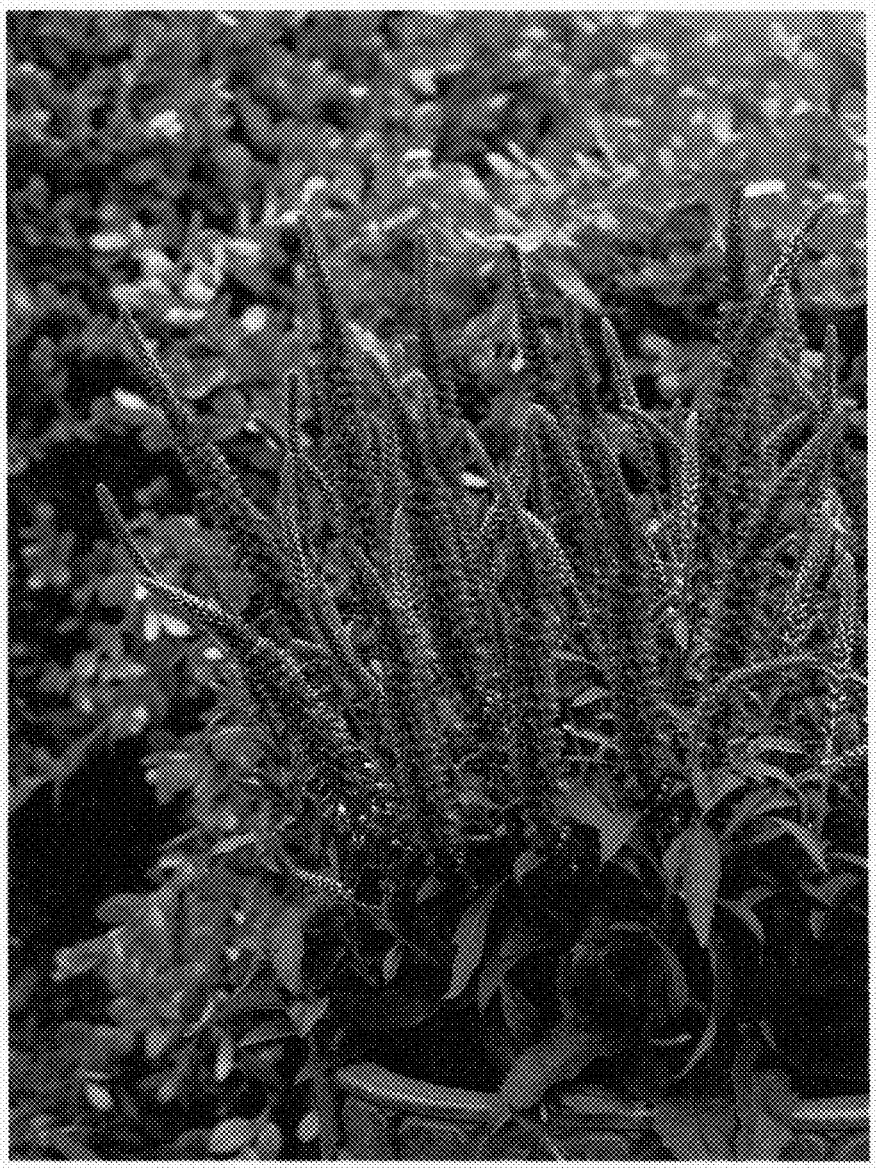

* * * * *